United States Patent
Valdes, Jr. et al.

(10) Patent No.: US 6,835,715 B1
(45) Date of Patent: Dec. 28, 2004

(54) MAMMALIAN DIHYDROOUABAIN-LIKE FACTOR AND THERAPEUTIC COMPOSITIONS

(75) Inventors: Roland Valdes, Jr., Simpsonville, KY (US); Hassan M. A. M. Qazzaz, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 09/503,559

(22) Filed: Feb. 11, 2000

Related U.S. Application Data

(60) Provisional application No. 60/119,921, filed on Feb. 12, 1999.

(51) Int. Cl.$^7$ .............................................. A01N 45/00
(52) U.S. Cl. ........................ 514/26; 424/537; 424/563; 424/570; 435/72; 514/21; 514/22; 514/23; 536/1.11; 536/5
(58) Field of Search .............................. 435/72, 73, 74, 435/1.73; 536/6.1, 5, 1.11, 4.1, 16.8, 16.9; 424/537, 563, 570; 514/21, 22, 23, 26

(56) References Cited

U.S. PATENT DOCUMENTS

| | | | |
|---|---|---|---|
| 5,429,928 A | 7/1995 | Blaustein et al. | 435/7.24 |
| 5,695,756 A | 12/1997 | Blaustein et al. | 424/130.1 |
| 5,844,091 A | 12/1998 | Blaustein et al. | 530/387.1 |

OTHER PUBLICATIONS

Hamylyn et al. Identification and characterization of a ouabain –like compound from human plasma, Proceedings of the National Academy of Sciences, (1991) vol. 88 pp. 6259–6263.*

Jacobs et al. The realashionship between the structure and the biological action of the cardiac glucosides. Journal of Biuological Chemistry (1927) vol. 74, pp. 287–294.*

Qazzaz et al., "A commercially available standard for dihydroouabain has two chromatographically distinct biologically active components," *Clinical Chemistry*, 1997, 43:S191.

Qazzaz et al., "Simultaneous isolation of endogenous digoxin–like immunoreactive factor, ouabain–like factor, and deglycosylated congeners from mammalian tissues," *Archives of Biochemistry and Biophysics*, 1996, 328:193–200.

El–Masri et al., "An antiserum for detection of a newly discovered dihydroouabain–like factor (Dihydro–OLF) isolated from mammals," *Clinical Chemistry*, 1999, 45:A82.

Qazzaz et al., "A newly discovered lactone–hydrogenated isomer (Dihydro–OLF) of mammalian ouabain–like factor (OLF) differentially inhibits the sodium pump," *FASEB J.*, 1999, 13:A1470.

Qazzaz, Hassan M., et al., "Secretion of a Lactone–Hydrogenated Ouabain–Like Effector of Sodium, Potassium–Adenosine Triphosphatase Activity by Adrenal Cells", *Endocrinology*, vol. 141, No. 9, (2000),3200–3209.

Qazzaz, Hassan M., et al., "Two Biologically Active Isomers of Dihydroouabain Isolated from a Commercial Preparation", *Biochimica et Biophysica Acta 1472*, (1999),486–497.

Zhao, Ning, et al., "Na, K– ATPase Inhibitors from Bovine Hypothalamus and Human Plasma are Different from Ouabain: Nanogram Scale CD Structural Analysis", *Biochemistry*, vol. 34, No. 31, (1995),9893–9896.

Qazzaz, et al., "Isolation of two chromatographically and biologically distinct components from a dihydrooubain commercial preparation", *FASEB J.*, 11(9), Abstract 1423, p. A1100 (1997).

* cited by examiner

*Primary Examiner*—Ulrike Winkler
(74) *Attorney, Agent, or Firm*—Fish & Richardson P.C., P.A.

(57) ABSTRACT

A novel mammalian dihydroouabain-like factor is disclosed which substantially fails to cross-react with mammalian ouabain-like factor (OLF) for binding to anti-OLF antibody, but cross-reacts with plant-related dihydroouabain (dho) for binding to anti-dho antibody, has maximal u.v. absorbance at 196 nm, has a non-peptidic, non-lipidic chemical structure and a fully hydrogenated lactone ring, has a concentration-dependent $Na^+,K^+$-ATPase (sodium pump) catalytic inhibitory activity which is 10-fold lower than OLF and 3-fold higher than plant-related dihydroouabain, and a high pressure liquid chromatography elution time about the same as dho. This factor is useful for therapy for congestive heart failure. An antibody and antibody fragments having affinity for mammalian Dh-OLF but not for OLF, and diagnostic and therapeutic methods comprise the antibody and means for quantifying the antibody and are useful for treating a condition caused by high level of OLF or Dh-OLF. Two isomers of plant-related dihydroouabain have been isolated. These compositions and methods are suitable for characterizing a variety of diseases and conditions associated with reduced sodium pump activity.

8 Claims, No Drawings

MAMMALIAN DIHYDROOUABAIN-LIKE FACTOR AND THERAPEUTIC COMPOSITIONS

This application claims the benefit of Provisional application Ser. No. 60/119,921, filed Feb. 12, 1999.

BACKGROUND OF THE INVENTION

1. Field of the Invention

This invention relates to the field of mammalian ouabain-like factors (OLF) and more particularly to a novel dihydroouabain like factor (Dh-OLF), and its use for the detection and treatment of conditions and diseases associated with regulation of the sodium-potassium pump, in particular for the detection and treatment of congestive heart failure. This invention also relates to those plant cardenolides that are cardiac glycosides. This invention also relates to antibodies and antibody fragments useful for the treatment of toxicity due to excess OLF or Dh-OLF.

2. Description of the Background

Digoxin and ouabain, plant cardenolides that are the two most commonly used cardiac gylcosides, are commonly administered to patients suffering from congestive heart failure because of their beneficial effect on cardiac contractility, that is, their positive inotropic effect. Positive inotropic effect generally refers to the enhancement of contractility of the cardiac cells in a dose-dependent manner. These drugs produce an increase in the force and velocity of ventricular contraction, and also a slowing of the heart rate. These two effects combine to provide a stronger heart beat. However, cardiac glycosides have narrow therapeutic indices and their use is frequently accompanied by toxic effects that can be severe or lethal.

The exact mode of action of cardiac glycosides is not completely known, but it is thought that the effects are mediated through regulation of the sodium pump. Abnormal sodium pump activity has been postulated to be involved in the pathophysiology of several diseases, including cardiovascular, neurological, renal, and metabolic disorders, among others. These complex effects may be related to the role of the pump in controlling the cellular ingress of other molecules.

The $NA^+,K^+$-ATPase enzyme or sodium pump is a membrane protein responsible for establishing an electrochemical gradient of $Na^+$ and $K^+$ ions across the plasma membrane of mammalian cells. The ion gradient formed by this enzyme is necessary for the active transport of essential nutrients into the cells, for regulation of osmotic balance and cell volume, and for maintaining the resting membrane potential in excitable cells. The $Na^+,K^+$-ATPase enzyme is the only known receptor for cardiac glycosides such as digitalis. The tight conservation of the digitalis binding site over many phyla, among other observations, suggests the existence of endogenous sodium pump inhibitors (SPIs) in mammals as well. These hypothetical mammalian inhibitors would be involved in modulating the activity of the sodium pump, and might be involved in vivo sodium homeostasis.

One of the side effects of administration of cardiac glycosides is arterial hypertension. It is thought that an excess of endogenous factors may also cause arterial hypertension, which is a risk factor in complications associated with various organs. Higher plasma levels of ouabain-like compounds (OLCs) were found in patients with primary aldosteronism and ectopic corticotrophin syndrome, two types of mineralocorticoid hypertension. In addition, 30–45% of patients with essential hypertension had increased plasma levels of OLCs and the blood pressures were statistically correlated with the OLC levels. Although presently available anti-hypertensive agents have proven beneficial, they still fall short of completely reversing the effects caused by high blood pressure. Accordingly, there still is a need for agents which are more specific and effective than those presently available in order to reverse the toxic effects of high levels of ouabain, whether administered or endogenous. It would be of further benefit to have a means of predicting the occurrence of hypertension in patients before the occurrence of organ damage due to sustained hypertension.

The kidneys have also been implicated in changes in blood pressure variations. A rise in blood pressure has been observed in clinical forms of hypertension, such as Liddle's syndrome, glucocorticoid-suppressible aldosteronism, and the syndrome of apparent mineralocorticoid excess, which appears to be closely related to a constitutive increase in sodium ($Na^+$) reabsorption in the kidney. Essential hypertension is a heterogeneous disease which is thought to result from genetic and environmental factors that interact to increase blood pressure, thus, gene mutations may also contribute to hypertension, and since these genes were shown to converge on a final common pathway, the result may be increased $Na^+$ reabsorption and/or decreased $Na^+$ excretion in the kidney. Although still uncertain, however, why increased $Na^+$ reabsorption might lead to high blood pressure, salt retention and plasma volume expansion trigger the secretion of sodium pump inhibitors (SPIs), which restore extracellular fluid volume via natriuresis. An increased secretion of SPIs, thus, may also elevate cytosolic $Ca^{2+}$ and produce vasoconstriction, which will account for the development and perpetuation of hypertension. Whatever the mechanism, it has been empirically noted that hypertension is associated with abnormal function of sodium regulation.

The chronic administration of ouabain has been shown to cause the development of hypertension in rats. Immunization of these Dahl salt-sensitive (S) rats against ouabain prevented a reduction in renal mass-saline hypertension and $Na^+$-induced hypertension.

Plant cardenolides, such as ouabain and digoxin, have been shown to bind specifically to highly conserved epitopes on the α-subunit of the $Na^+,K^+$-ATPase enzyme (sodium pump) and to stabilize the phosphorylated intermediate. This effect leads to the inhibition of pump-associated transport of sodium, potassium and other important biologic compounds across cell membranes. It has furthermore been postulated that a hormonal-axis may regulate the activity by mammalian ligands similar to plant cardenolides of the sodium pump. Two types of mammalian compounds have been found to date with properties similar to those of plant cardenolides: (1) digoxin-like factors such as DLF or DLIF, and (2) ouabain-like factors such as OLF or HIF. The DLIF family includes a series of deglycosylated species and Dh-DLIF, a dihydrodigoxin-like isomer. Cytochrome $P_{450}$ was recently shown to mediate the conversion of dihydrodigoxin, a plant cardenolide of low DLIF immunoreactivity, to one with high DLIF immunoreactivity. This suggests a possible in vivo metabolic conversion of Dh-DLIF, a less active dihydro-species, to DLIF, a more biologically active species. The present inventors have recently reported the presence of a deglycosylated species of human OLF analogous to the plant ouabain. Dihydroouabain (dho), the chemically-reduced form of ouabain having a saturated lactone ring, has been used to study the biological activity of ouabain and its interaction with the sodium pump.

The chemical formulas of ouabain and dihydroouabain are shown below.

Ouabain Dihydroouabain
$C_{29}H_{44}O_{22}$ $C_{29}H_{46}O_{12}$
MW 584 MW 586

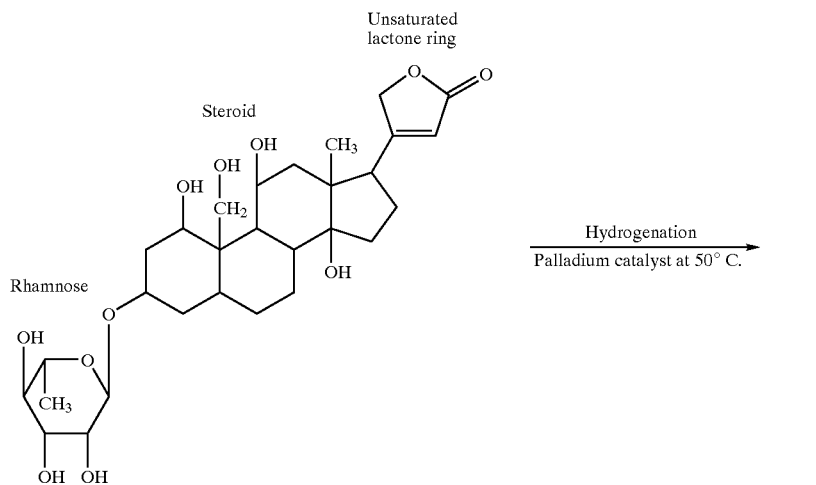
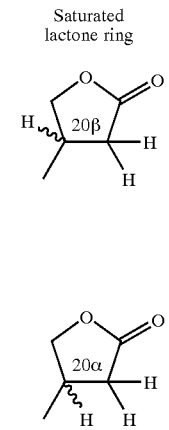

Ouabain contains an aglycone consisting of a steroid nucleus with an unsaturated lactone ring attached at the $C_{17}$ position, a sole sugar molecule, a rhamnose, attached at the $C_3$ position. The only difference between ouabain and dihydroouabain (dho) is that the latter has a fully hydrogenated lactone ring.

In general, the reduced lactone ring forms of both digoxin and ouabain show relatively lower potencies than their oxidized counterparts for inhibiting $Na^+,K^+$ pump catalytic activity. However, they have other biophysical properties, such as being rapidly washed out from tissues, etc. that are rather advantageous.

Antibodies to specific molecular structures may be made by immunization of animals such as mice or rabbits with the target structure by methods known in the art. Non-human antibodies, including polyclonal and monoclonal antibodies, raised against specific human molecules have been used for diagnosis and therapy as is known in the art. Chimeric antibodies are direct fusions between variable domains (the reactive portion or complementary determining region or CDR) of one species and constant domains (framework region, FR) of another. Murine/human chimeric antibodies, in which mouse CDR is fused to human FR, have been shown to be less immunogenic in humans than whole murine antibodies. The size of the bioactive molecule may also be reduced, so as to increase the tissue target availability and to allow for ultimate excretion through the kidneys of the antibody, by removing most of the heavy and light chain constant regions to form an $F_v$ antibody, which is basically an isolated CDR. Although any species may be used for the production of antibodies, when large quantities of antibody are required, it is advantageous to use large animals such as sheep, goats or horse. However, any mammal may be used. Antibodies or fragments from either polyclonal or monoclonal sources may be purified by affinity separation. Common to all of these potentially therapeutic forms of antibody are the required CDRs, which guide the molecule to its ligand.

The development of immunoassays has permitted the utilization of antibodies for diagnostic purposes, in particular, for the determination of levels of different endogenous agents in animal and human tissues. Immunoassays rely on the quantitative binding of a known amount of a known antigen to a known amount of antibody, on the binding of this antibody to the antigen to be used as a standard, and on a comparison of the latter to the amount of unknown analyte in a sample which is bound by the same antibody. When both reactions are conducted in the same medium, analyte present in the unknown sample interferes with the binding of known quantities of antibody to known quantities of antigen. A key step of these assays is the separation of bound antibody or antigen from the unbound antibody or antigen. Many configurations for this reaction are well known, either as direct immunometric, competitive or displacement assays, and the like. Quantitative results are generally obtained through hemagglutination assays, radioimmunoassays, enzyme-linked assays, and the like.

In an immunoassay, a given analyte present in a animal or human tissue is compared to a known quantity of the solubilized standard analyte. The most common tissue analyzed is blood, and more specifically serum and/or plasma from blood, but urine, cerebrospinal fluid, different serum preparations and different animal and human tissues and fluids are also routinely assayed. In endocrinology and clinical chemistry, enzyme-linked assays and radioimmunoassays have been used to determine levels of hormones, proteins and lipid metabolites, among other substances. Levels of certain molecules in the blood or other tissue may be indicative of a disease state, often at a very early stage before symptoms are manifest. These molecules are termed markers of the condition.

Accordingly, there still exists a need for an assay to detect the presence of markers indicative of sodium pump function, particularly such an assay that is fast, cost effective and which may be conducted without highly specialized personnel. This technology would be immediately applicable to the screening of populations at risk as well as of patients undergoing treatment for diseases requiring control of sodium pump function.

SUMMARY OF THE INVENTION

This invention relates to a purified, isolated mammalian dihydroouabain-like factor (Dh-OLF) that inhibits the sodium pump ($Na^+,K^+$-ATPase), and is a pro-drug for the mammalian ouabain-like factor (OLF), to which it is converted in vivo. Conversely, OLF is a pro-drug for Dh-OLF, to which it is converted in vivo. Although Dh-OLF has an hydrogenated lactone ring, as does the plant derived dihydroouabain (dho), the factor of the invention has other characteristics which set it apart from dihydroouabain. The Dh-OLF has a molecular weight of about 586 and substantially fails to cross-react with mammalian ouabain-like $Na^+$, $K^+$-ATPase inhibitory factor (OLF) for binding to anti-ouabain antibody. It is significant that it cross-reacts with plant dihydroouabain (dho) for binding to anti-dho antibody. The deglycosylated compounds show a similar immunoactivity pattern as the sugar-containing factors, suggesting that the major antigenicity resides in the lactone moiety. Therefore, for purposes of describing this invention, OLF, Dh-OLF, ouabain and dho are intended to include their deglycosylated analogues. "Dho" is comprised of isomers dho-A and dho-B. Dh-OLF has maximal uv absorbance at 196 nm, a non-peptidic chemical structure as evidenced by lack of absorbance at 280 nm, a non-lipidic chemical structure as evidenced by lack of lipase digestion and lack of staining with a lipid stain, a fully hydrogenated lactone ring; 10-fold lower potency than OLF and 3-fold higher potency than plant dihydroouabain-B (dho-B) for inhibiting $Na^+,K^+$-ATPase catalytic activity, 10-fold lower potency than OLF and 3-fold higher potency than plant dho-B for phosphorylating $Na^+,K^+$-ATPase $\alpha$ subunits, a concentration-dependent inhibition of $Na^+,K^+$-ATPase catalytic activity; a concentration-dependant phosphorylation of $Na^+,K^+$-ATPase $\alpha$ subunits, and a high pressure liquid chromatography elution pattern about the same as dihydroouabain.

The endogenous ouabain-like factors (OLF and Dh-OLF) may be isolated by a method involving the use of uv spectrophotometry, preparative high pressure liquid chromatography or affinity separation with antibodies or other binding agents that are specific to them or to ouabain or dihydroouabain.

This invention also relates to monoclonal and polyclonal antibodies and fragments thereof and to their use for the detection of Dh-OLF and/or OLF in biological (animal) samples to make an early assessment of disease states associated with abnormal levels of Dh-OLF or abnormal ratios of Dh-OLF to OLF. The antibodies or, preferably, fragments thereof, are also suitable for therapeutic use in the treatment of various diseases associated with increased levels of Dh-OLF, including metabolic diseases, heart disease, high blood pressure, renal impairment, neurologic disorders such as Alzheimer's disease, psychiatric conditions, ophthalmic diseases, and sexual dysfunction, among others. Monoclonal antibodies, if desired, may also be made by methods well known in the art.

In addition, this invention also provides an in vivo method for reducing levels of of Dh-OLF or OLF by administration to a subject in need of the treatment of a prophylactically or therapeutically effective amount of the antibody of the invention or an anti-dho antibody or, preferably, fragments of these antibodies. Other specific binding agents are known, such as synthetic compounds such as aptomers. All such specific binding agents which bind ouabain or dihydroouabain or their endogenous analogues can likewise be use in this method.

The levels of Dh-OLF and/or OLF present in a test sample may be assessed with the aid of a diagnostic assay of this invention that relies on the selective binding of the factor by an antibody having affinity for this compound or dho isomer mixture, and the subsequent addition of a labeled antibody Fc-binding agent to generate a signal which is linearly correlatable with the amount of Dh-OLF present in the biological sample.

The levels of Dh-OLF and/or OLF present in a test sample may alternatively be assessed by quantitative HPLC, where the elution peaks are compared to the peaks derived from a known amount of Dh-OLF and/or OLF. The hydrogenation of ouabain using palladium catalyst at 50° C. produces two isomers (dho-A and dho-B). The elution peaks thought to be Dh-OLF of a test sample may be compared to the peaks derived from a known amount of dho-B and the concentration of Dh-OLF estimated from comparison of the respective peak heights.

It is known that the ratio of OLF to Dh-OLF or OLF to Dh-OLF may vary from subject to subject. This variation of ratio is thought to be due to a variable rate of interconversion of Dh-OLF and OLF. Since OLF has ten-fold the activity of Dh-OLF on the activity of the sodium pump, the conversion enzyme(s) will provide a novel target for the development and testing of antihypertensive or antihypotensive drugs.

A more complete appreciation of the invention and many of the attendant advantages thereof will be readily perceived as the same becomes better understood by reference to the following detailed description when considered in connection with the accompanying figures. While the compositions and methods of this invention have been described in terms of preferred embodiments, it will be apparent to those skilled in the art that certain substitutes and modifications may be made without departing from the spirit and scope of this invention as defined by the appended claims.

DESCRIPTION OF THE PREFERRED EMBODIMENTS

This invention arose from a desire by the inventors to improve on prior technology for the prevention and treatment of diseases and conditions associated with dysfunction and/or regulation of function of the sodium/potassium pump. Prior therapeutic agents are either too potent, too long lasting and/or their effects are hard to modulate. In their search, the present inventors determined the existence of, and isolated and characterized, a mammalian dihydroouabain-like factor (Dh-OLF) of unique properties. Although Dh-OLF has an hydrogenated lactone ring, this factor has other characteristics which set it apart from dihydroouabain. Dh-OLF was isolated with the aid of UV-spectrophotometry, cross-reactivity with antibodies specific to both ouabain and dihydroouabain (dho) and two independent in vitro bio-assays: inhibition of the catalytic activity of the $Na^+,K^+$-ATPase enzyme and phosphorylation of the $Na^+,K^+$-ATPase enzyme $\alpha$-subunits. The mammalian Dh-OLF of the invention was found to co-migrate on HPLC with one unique isomer of the plant derived dihydroouabain (dho), to exhibit a maximal absorbance peak at 196 nm, to exhibit a substantially reduced molar absorptivity when compared to OLF at 220 nm, to inhibit sodium pump activity ($Na^+,K^-$-ATPase enzyme) and phosphorylate the enzyme in a concentration-dependent manner, and to react with antibody specific to dihydroouabain but not with antibody specific to ouabain. However, unlike dho, Dh-OLF upon dehydrogenation showed only one isomeric peak.

The mammalian Dh-OLF of this invention was found by the inventors to be about 10-fold less potent ($IC_{50}$=590 mM) for inhibiting the catalytic activity of the $Na^+,K^+$-ATPase enzyme than OLF ($IC_{50}$=60 nM), its oxidized counterpart. In addition, the present agent was also found to be about 3-fold more potent for inhibiting the catalytic activity of the same enzyme than one of the isomers of dihydroouabain (dho-B; $IC_{50}$=1700 nM), which is of plant origin. The ability of the present agent to enhance the phosphorylation of the alpha-subunit of the sodium pump was found to be concentration dependent.

The inventors were able to isolate Dh-OLF from bovine adrenal cortex (yield=about $0.36\pm0.34\times10^{-10}$ moles/g), and from human serum (yield=about $50\pm0.46\times10^{-10}$ moles/l). In the experimental disclosure provided below, the inventors show Dh-OLF to be far more abundant than endogenous OLF in the same tissues. They found the proportion of Dh-OLF:OLF to be about 22 in bovine adrenal cortex, and about 13 in human serum. The existence of a mammalian Dh-OLF provides, by itself, a clear in vivo metabolic bridge to the boosting or reduction of endogenous OLF levels. Furthermore, it is shown that the ratio of OLF to Dh-OLF, or vice-versa, varies from subject to subject and in an individual subject at different times. The present agent, thus, is suitable also for use as a pro-drug which, when administered to a subject, is converted in vivo into OLF. The present discovery makes it possible to modulate an endogenous mammalian regulatory hormonal axis which, itself, is primordial to the control of the activity of the sodium/potassium pump.

The results of various experiments on ouabain-stimulated Pi-phosphorylation of the α-subunit of the $Na^+,K^+$-ATPase show the importance of ouabain's binding to a specific binding site on the α-subunits. The inhibition of the sodium pump by ouabain and other plant-derived cardiac glycosides and mammalian sodium pump inhibitors brings about a decrease of ATP break-down. While many other stimulants of ATPase activity such as the $Ca^{++}$-ATPase, also typically bind other tissue ATPases, the ouabain-stimulated phosphorylation is specific for the $Na^+, K^+$-ATPase, and thus avoids such interference. Unlike the endogenous ouabain-like factors, plant-derived dho, in fact, has about 82% of the phosphorylation activity of plant-derived ouabain, at equimolar concentrations, for the ouabain stimulatable phosphorylation of the sodium pump. In this phosphorylation, phosphate (Pi) is incorporated covalently into the same aspartyl amino acid of the α-subunit of the $Na^+,K^+$-ATPase that is phosphorylated by ATP during ATP-hydrolysis. Both OLF and Dh-OLF, isolated from bovine adrenal cortex and human plasma, stimulate phosphorylation by incorporating Pi into the α-subunit of the $Na^+,K^+$-ATPase. The OLF and Dh-OLF stimulated incorporation of Pi is highly dependent on the concentration of these factors. The concentration of Dh-OLF required for phosphorylation (estimated from the density of the gel bands) parallels the concentration range of $Na^+,K^+$-ATPase required for inhibition of the activity of the sodium pump enzyme. However, unlike the plant analogues, which have similar activities, OLF has ten-fold the activity of Dh-OLF.

All dihydro species may be produced in vitro by hydrogenation of the corresponding cyclopentenolide lactone ring of the plant oxidized-species, e.g. ouabain, digoxin, digitoxin, etc., using either platinum oxide catalyst at room temperature or palladium-carbon catalyst at 50° C. The hydrogenation of the lactone ring linkage produces a second center of asymmetry at C-20. Dihydroouabain also has been shown by the inventors to have two isomers: dho-B and dho-A. In contradistinction, OLF only appears to have one dihydrogenated species, Dh-OLF, in mammalian tissues. This patent provides clear evidence that the Dh-OLF obtained from bovine adrenal cortex and human plasma is homogeneous. The inventors have also characterized the binding of OLF and Dh-OLF to anti-ouabain and anti-dihydroouabain antibodies by U.V. spectra and chromatographic mobility. The data provided below show the quantitative ratio and molar concentrations of both factors in human serum. The adrenal glands are a rich source of both Dh-OLF and OLF. The data provide a clear view of the metabolic and physiopathological interrelation of OLF and Dh-OLF on one hand, and of DLIF and Dh-DLIF on the other, and the link to their production and regulation to the adrenal gland. A similar endogenous factor, dihydrodigoxin-like factor (Dh-DLIF) has been shown to be metabolized to a digoxin-like immunoreactive agent by microsomes from bovine adrenal cortex. Qazzaz et al. (1996) Clinical Chemistry 42:1092, 1099. Dh-OLF may be exogenously administered as a pro-drug, and be metabolically transformed to OLF in vivo. Conversely, OLR may be administered as a pro-drug of Dh-OLF.

The oxidation/reduction state of the lactone ring of the Dh-OLF/OLF pair plays a central role in the interaction with the $Na^-,K^+$-ATPase receptor. Recent evidence suggests that other dihydro-species, such as dihydro-digoxin, have affinity comparable to that of digoxin for binding to specific isoforms of $Na^+,K^+$-ATPase. Dh-OLF, on the contrary, is less biologically active than the oxidized form, in contrast to the plant derived dho, which has similar (82%) activity as plant-derived ouabain. The metabolic link of Dh-OLF to OLF in the adrenal glands provides a real opportunity to utilize Dh-OLF as a pro-drug for the in vivo formation of OLF and its secretion into the circulation. The conversion step provide a novel target for treating hypertension by preventing the conversion of Dh-OLF to the ten-fold more active OLF. Hypotension may be treated by stimulaitng the conversion of Dh-OLF to OLF.

Conversely, OLF will form Dh-OLF by bacterial conversion in the gut, which will then be absorbed into the circulation. OLF may be present in the gut either from oral administration of OLF or from excretion of OLF from blood into gut, with conversion to Dh-OLF and subsequent reabsorption. There is clearly a balance which may be modulated by the in vivo conversion of endogenous OLF to Dh-OLF, and or Dh-OLF to OLF. Thus, their relative abundance in the adrenal cortex or in a specific tissue or organ may be modulated by administration of Dh-OLF or anti-Dh-OLF antibody or by other compounds that affect the interconversion of these analogues.

The present invention, thus, provides a purified, isolated mammalian dihydroouabain-like factor (Dh-OLF), of molecular weight of about 586, and has a fully hydrogenated lactone ring with maximal uv absorbance at 196 run, a non-peptidic chemical structure as evidenced by lack of absorbance at 280 nm, and a non-lipidic chemical structure as evidenced by lack of lipase digestion and lack of staining with a lipid stain. In addition, Dh-OLF has a high pressure liquid chromatography (HPLC) elution pattern similar to dihydroouabain (dho), cross-reacts with plant dihydroouabain (dho) for binding to anti-dho antibody but substantially fails to cross-react with mammalian ouabain-like factor (OLF) for binding to anti-OLF antibody. The factor inhibits $Na^+,K^+$-ATPase activity with 10-fold lower potency than OLF and 3-fold higher potency than plant dihydroouabain-B (dho-B), and phosphorylates $Na^+,K^+$-ATPase α-subunits with 10-fold lower potency than OLF and 3-fold higher potency than plant derived dihydroouabain-B (dho-B). The Dh-OLF of the invention inhibits $Na^+,K^+$-ATPase catalytic activity and phosphorylates $Na^+,K^+$-ATPase α-subunits in a concentration-dependant manner. The factor of this invention is available in different purities, for example, 90%, 95%, and even 99% pure. A more purified form of the factor may be obtained by affinity separation with the anti-Dh-OLF antibody of this invention. The factor may be provided in freeze-dried or lyophilized form as a powder, or in the form of a solution.

The presently reported finding relates to a mammalian factor, which may be of primate origin, whether human or non-human simian, bovine, ovine, murine, equine, rabbit, goat, bovine, and guinea pig origin, among others. For human use, preferred are the factors of human and bovine origin. However, others may also be utilized. The mammalian Dh-OLF factor described here is easily converted to OLF in vivo and in vitro. OLF likewise may be converted to Dh-PLF in vivo and in vitro. Thus, each may be administered as a pro-drug for the other. Oxidation, for instance, may occur with cytochrome $P_{450}$ in the presence of NADPH, and an NADPH-dependant reductase. The mammalian Dh-OLF factor is easily obtained by bacterial reduction of OLF by anaerobic, faculative anaerobic or aerobic bacteria. It has been found that *Eubacteria* spp. are particularly useful for this reduction. In the laboratory, the reduction may be attained by hydrogenation of OLF with $H_2$ with the aid of a catalyst as is known in the art.

The factor of the invention is also provided in the form of a composition, preferably combined with a pharmaceutically or veterinarily acceptable carrier. Pharmaceutical compositions for use in the present invention include systemic and topical formulations, and among these preferred are formulations which are suitable for inhalation, oral, rectal, vaginal, nasal, ophthalmic, optical, intracavitary, intraorgan, or other modes of therapy.

A preferred formulation is an oral formulation comprising an oral carrier, the composition, and optionally an enteric coating. Enteric coatings are known in the art as are their components and methods for preparing them and, thus, need not be described in this patent. Another preferred formulation is a sub-lingual formulation comprising the composition, wherein the flavoring and inert diluent are selected from the group consisting of sucrose, acacia, tragacanth, gelatin and glycerin. Other carriers and diluents may be utilized as will be known to an artisan. This patent also provides a parenteral formulation comprising the composition comprising a solution, suspension or emulsion of the factor, and optionally other agents as well as described below. These amounts may be adjusted when and if additional agents with overlapping activities are included as discussed below.

The dosage will vary depending on age, weight, and condition of the subject. Treatment may be initiated with small dosages containing less than optimal doses of the agent of the invention, be it the factor or one of its salts, and increased until a desired, or even an optimal effect under the circumstances, is reached. In general, the dosage is about 1 µg/kg up to about 100 µg/kg body weight. Currently, preferred are dosages of about 2 µg/kg to about 50 µg/kg body weight of the subject, still more preferred are dosages of about 8 µg/kg to about 35 µg/kg body weight of the subject. Higher or lower doses, however, are also contemplated and are, therefore, within the confines of this patent. A medical practitioner will know to prescribe a small dose and observe the effect on the subject's symptoms. Thereafter, he/she may increase the dose if suitable. In general, the active agent is preferably administered at a concentration that will afford effective results without causing any unduly harmful or deleterious side effects, and may be administered either as a single unit dose, or if desired in convenient subunits administered at suitable times throughout the day.

The treatment of heart disease associated with dysfunction of the sodium pump, for example, congestive heart failure, atrial fibrillation, arrhythmias, and others, may also be undertaken with a prophylactically or therapeutically effective amount of the agent. The present treatment is of particular help in the treatment of congestive heart failure.

The factor of this invention also may be applied to prophylactically or therapeutically treat various diseases and conditions associated with abnormal levels of sodium pump activity. One example is the treatment of hypertension by administration of a prophylactically or therapeutically effective amount the factor to relieve the symptoms and consequences of prolonged periods of high blood pressure. The method of this patent is suitable for treating various types of hypertension, such as essential hypertension, thyroidism-induced hypertension, and pregnancy induced or associated hypertension.

Cataracts are also treatable by administration of a prophylactically or therapeutically anti-cataract effective amount of the antibody. The treatment may be applied to slow the progress of cataracts, to prevent them in the elderly, or to avoid a recurrence after cataract surgery. The dose of the factor is typically custom tailored to each patient, and the patient's eyes, as a medical doctor would know.

The agent is also suitable for treating sexual dysfunction, particularly in males, by administration of a prophylactically or therapeutically effective amount of Dh-OLF.

This agent is also active for delaying and treating Alzheimer's disease and, as in the case of cataracts and high blood pressure, it is most effective when administered in prophylactic form at the first signs of the disease.

More generally, the present method is applicable to increasing the in vivo levels of Dh-OLF and OLF by administration of a prophylactically or therapeutically factor elevating effective amount of Dh-OLF or of OLF. As described above, each acts as a pro-drug for the other, because of the interconversion of the two in vivo. For example, Dh-OLF is converted in vivo to OLF, which agent has a greater potency for inhibiting the sodium pump. Thus, some of its effect is attained by direct action, and the rest by its conversion to OLF, which provides a greater potency to the agent.

When lowering of OLF and Dh-OLF is desired, antibodies that have affinity for the mammalian Dh-OLF may be developed and $F_v$ fragments may be made. These antibodies or fragments may selectively bind Dh-OLF but not OLF, and more preferably they have specificity for Dh-OLF but substantially lacks affinity for either OLF or plant derived ouabain. The antibody of this invention is presented in the form of polyclonal antibody, which is raised by administration of the Dh-OLF to an animal such as a rabbit and isolated by methods known in the art. Because of the cross-reactivity found by these inventors, antibodies to Dh-OLF may also conveniently be raised by administration of the plant dho, dhoA,dhoB or deglycosylated analogues to an animal such as a rabbit. In another embodiment, the antibody is a monoclonal antibody, which may be obtained, for example, by methods well known in the art. $F_v$ fragments may be made from either polyclonal or monoclonal antibodies. Techniques for obtaining monoclonal and polyclonal antibodies, or fragments or synthetic analogues thereof are known in the art.

The anti-Dh-OLF antibody is typically administered in dosage based upon the levels of OLF or Dh-OLF in the subject and the degree to which reduction of these levels is desired. The common ranges are from 1 mg to 2 gm, more preferably 10 mg to 1.5 gm, and still more preferably 15 to 800 mg per kg body weight of the subject.

Also provided by the inventors is a diagnostic kit, that comprises Dh-OLF or plant derived dihydroouabain (dhoB) isomer as a standard, the anti-Dh-OLF antibody or anti-dho antibody, and instructions for use of the kit with an antibody Fc-binding agent and a label in determining the presence of Dh-OLF in a sample. The diagnostic kit may also optionally contain an antibody Fc-binding agent, a label, and instructions for operatively linking the label to the anti-Fc antibody. Alternatively, when the label to be utilized has a limited half life, it may be purchased at the end use point. The antibody Fc-binding agent for use with this invention may be anti-Fc antibody or binding fragments thereof, protein A or protein C, among others. The label for use with the agent of the invention may be any detectable label, such as a radio-, fluorescent, phosphorescent, or bioluminescent labels, or enzyme-substrate combinations, among others known in the art. The kit may also be provided with one or multiple solid substrate units for conducting an in vitro assay, as well as substrate background lowering coating materials.

The presence of the Dh-OLF of the invention in an animal sample suspected of containing Dh-OLF analyte may be qualitatively determined by contacting the test sample with a solid substrate-bound antibody having specificity for Dh-OLF or for a plant derived dihydroouabain (dho) isomer mixture but not for OLF or ouabain, under conditions effective for the antibody to bind any analyte present in the sample and form antibody-analyte complex(es), contacting the substrate-bound antibody-analyte complex(es) with a labeled antibody Fc-binding agent, under conditions effective to bind to any substrate-bound analyte-antibody complex(es) to form a solid substrate-bound analyte-anti-Dh-OLF antibody-antibody Fc-binding agent or analyte-anti-dho isomer mixture antibody-antibody Fc binding agent labeled complex(es), and detecting the amount of solid substrate-bound label. The antibody utilized may be anti-Dh-OLF, anti-dho antibody or a mixture of both, and each one may be a polyclonal mixture or a monoclonal antibody. These are obtained as is known in the art and referenced above. The method may further include a comparison of the amount of labeled complex(es) obtained for the test sample to the amount of complex(es) obtained for a known amount of a standard, e.g. Dh-OLF or plant derived dihydroouabain (dho) isomer mixture under the same or similar conditions. This may be attained, for example, by comparing the amount of labeled complexes obtained for the analyte to the amount of labeled complex(es) obtained for one or more known amounts of the standard Dh-OLF or dho mixture under the same or similar conditions. In one embodiment, the known amount of standard Dh-OLF or dho mixture may be added to the test sample prior to measuring the amount of labeled complex(es) obtained with and without the standard Dh-OLF or dho mixture. However, other assaying modes such as quantitative HPLC are also suitable.

The methods of this patent may suitably be practiced with samples of any body fluids and tissues, including blood, serum, cerebrospinal fluid (CSF), saliva, pleural or synovial fluid and bone marrow, among others. When the test sample, for example, is blood, it is necessary to separate the serum from the rest of the sample. Typically, all labels utilized for this type of assay are suitable. Examples are radio-, fluorescent, phosphorescent and bioluminescent labels, and enzyme-substrate and other combinations known in the art. In one embodiment, the label may be operatively linked to the antibody Fc-binding agent via a linker. The label, however, may also be linked to an Fc-binding agent which is administered separately but binds to the antibody. Generally, the binding of the antibody to the analyte and the standard molecule is allowed to proceed for a pre-determined period of time, and then stopped. The Dh-OLF- or dho-binding antibody may be a polyclonal or monoclonal antibody, and preferably fails to bind to OLF and ouabain. The present invention also provides a treatment for patients afflicted with impaired renal function by administration of a prophylactically or therapeutically effective amount of the antibody or fragments or synthetic analogues thereof. The present treatment may be continued for prolonged periods of time in cases where renal impairment persists or renal failure is highly probable. More generally, the present method is applicable to the reduction of organ secretion of Dh-OLF or OLF by administering to a subject in need of the treatment an Dh-OLF or OLF organ secretion reduction effective amount of the antibody of the invention. The antibody of the invention, chimeric antibody, and humanized antibody show substantially no strong binding to normal tissue. The rabbit and murine antibody show a pattern similar to that of the chimeric polypeptide and the humanized antibody. In one preferred embodiment, the antibody of the invention is labeled.

Having now generally described this invention, the same will be better understood by reference to certain specific examples, which are included herein for purposes of illustration only and are not intended to be limiting of the invention or any embodiment thereof, unless so specified.

EXAMPLES

Example 1

Chemicals and Reagents

All chemicals used were reagent grade. 5-sulfosalicylic acid (SSA), calcium carbonate ($CaCO_3$), digoxin, ouabain, ouabagenin, dihydroouabain, porcine cerebral cortex $Na^+$, $K^+$-ATPase (PCC), all reagents for catalytic inhibition of the sodium pump (adenosine 5'-triphosphate (ATP), ammonium molybdate, tween-80, bovine serum albumin (BSA), and all reagents for gel electrophoresis e.g., acrylamide, bis-acrylamide, N,N,N',N'-tetramethyl-ethylene diamine (TEMED), Tris [Hydroxymethyl]aminomethane (TRIZMA base), sodium dodecyl sulfate (SDS), glycine, β-mercaptoethanol, bromophenol dye) except ammonium persulfate, which was purchased from Amresco (Solon, Ohio), were obtained from Sigma (St. Louis, Mo.). Digoxigenin and dihydrodigoxin were donated by Burroughs Wellcome Co. (Research Triangle Park, N.C.). Pre-stained protein markers were purchased from Bio-Rad (Richmond, Calif.). Phosphorus-32-phosphate ($^{32}Pi$, 1 mCi in 100 $\mu L$) was purchased from NEN, Life Science Products (Boston, Mass.). Sulfuric acid ($H_2SO_4$) and hydrochloric acid (HCl) were obtained from Fisher (Fair Lawn, N.J.). Acetonitrile ($CH_3CN$) and perchloric acid ($HClO_4$) were both chromatographic-grade and obtained from Aldrich Co. (Milwaukee, Wis.). TMB soluble reagent and TMB stop buffer were purchased from SKYTEK Laboratories (Logan, Utah) Deionized water ($dH_2O$) was used for all manipulations of biological materials.

Example 2

Equipment and Materials

A Polytron PT 3000 (Brinkman, Westbury, N.Y.) was used for homogenizing adrenocortical tissue and an Orion pH/SE meter model 710A (Orion, Cambridge, Mass.) for pH measurements. Solid phase extraction C-18 cartridges (Sep-Pak) were obtained from Waters Associates (Milford, Mass.). HPLC was performed on C-18 reverse-phase $\mu$ Bondapak columns (3.9×300 mm, 10-$\mu$m particle size) connected to a Waters 600E system controller and a Waters 966 photodiode array detector. Eluted fractions were collected with a Waters Fraction Collector from Millipore Corp. (Millford, Mass.) and evaporated with a Jouan Centrifugal Vacuum Concentrator RC 10.22 connected to a Jouan Refrigerated Trap RCT 60 (Winchester, Va.). For UV-spectrophotometry, we used a Hewlett-Packard (Palo Alto, Calif.) Model 8452A diode array spectrophotometer. A Beckman JA-2 centrifuge (Beckman, Palo Alto, Calif.) was used for centrifugation in the tissue preparation procedure. For sodium pump inhibition assays, we used disposable non-sterile 96-well flat-bottom polystyrene microtiter plates purchased from Corning (Corning, N.Y.) and the color development was measured at 340 nm on a DuPont Microplate Reader II, Multiskan MCC/340, (Wilmington, Del.).

Monoclonal mouse anti-rabbit NKA isoform-specific antibodies purchased from Upstate Biotechnology Inc. (UBI, Lake Placid, N.Y.) were used for western blots. Goat anti-mouse horseradish peroxidase-conjugate antibody was purchased from Bio-Rad (Hercules, Calif.), and used as the second antibody in the detections of both the sodium pump isoforms by western analysis and dho by enzyme immunoassay (EIA).

Gel electrophoresis was applied to resolve the proteins of interest and performed on both a minigel and a vertical slab gel electrophoresis units from Hoefer Scientific Instruments (Model SE 245, SE 260 and SE400, San Francisco, Calif.). Acid gels were dried on a Slab Gel Dryer (SDG 4050) connected to a Savant Gel pump (GP100) (Farmingdale, N.Y.). Densitometry measurements of the $^{32}$Pi-radiolabeled bands were performed on a Personal Laser Densitometer, SI (Molecular Dynamics, Sunnyvale, Calif.). For cross-reactivity studies a ouabain EIA reagent kit was purchased from NEN Research Products (Boston, Mass.).

Example 3

Tissue Preparation

Bovine adrenal glands were obtained from Pel-Freeze Biologicals (Rogers, Ark.) or provided by a local abattoir. The cortices were separated from medulla, sliced, chopped and homogenized in 2 ml $dH_2O$ g cortex using a Polytron PT 3000 homogenizer. The homogenate was centrifuged three times at 34,000 g for 30 minutes at 4° C. after which the pellet of each centrifugation step was resuspended in $dH_2O$ (1 ml/g cortex). The proteins in the tissue homogenates were precipitated by incubating the supernatant with 1% SSA at room temperature for 60 sec with continuous stirring followed immediately by adding an excess amount of $CaCO_3$ until the pH increased and remained at 5.2. This extract was then centrifuged at 80,000×g for 10 min at 4° C. followed by vacuum filtration using two layers of Whatman #1 filter paper. Initial purification was performed by solid-phase extraction. The C-18 reversed-phase solid phase Sep-Pak extraction cartridges (Vac 10 cc) were primed with 1 vol $CH_3CN$ followed by rinsing with 2 vol of deionized $dH_2O$. The supernatant was loaded and passed through the cartridge twice at a rate of 1 ml/min. The cartilage was then washed twice with 2–4 vol of $dH_2O$ (typically 20–30 ml) before the compounds of interest were eluted with 20 ml of 10% $CH_3CN$ in $dH_2O$. To remove the $CH_3CN$, the eluates were evaporated to dryness in a vacuum desiccator, reconstituted in $dH_2O$, and passed through a 0.22 micron filter from Whatman (Clifton, N.J.) for removal of particulates.

Example 4

HPLC Reverse-Phase Chromatography

In the first chromatographic step the reconstituted Sep-Pak eluates were fractionated by high pressure liquid chromatography (HPLC) using a linear $CH_3CN:H_2O$ gradient of 20–80% over 30 min. (1 ml fraction/min were collected for 40 min). Typically, fractions of interest eluting around 6 min were collected, evaporated, reconstituted in 1 ml of $dH_2O$, and measured by either digoxin-RIA or ouabain-EIA prior to any further analysis. To ensure proper separation of the compounds of interest, these steps were repeated until all the eluate from the previous extraction step was analyzed. In the second chromatographic step, an isocratic mode of 10% $CH_3CN$ in water was utilized to separate ouabain and its two congeners (ouabagenin and dihydroouabain) from each other. To separate OLF and its congeners, the fraction eluting at 6 min. from the first chromatographic step was further chromatographed using a similar mobile phase of an isocratic-mode of 10% $CH_3CN$ over 40 minutes. Fractions (1 ml/1 min) were collected, evaporated, reconstituted in $dH_2O$ and measured by ouabain EIA and UV-spectrophotometry at 220 and 196 nm. The fractions eluting at 19, 24.5, 27.5, and 30.5 min were re-chromatographed on the same isocratic mode for additional purity. These purified fractions were analyzed again by ouabain EIA and dihydroouabain EIA for OLF and Dh-OLF respectively, and the absorbance at 196 and 220 nm was measured. The final yield of OLF and its related congeners were determined using the measured UV absorbance and their (ouabain and or dihydroouabain) immunoreactive equivalent concentrations.

Example 5

Human Serum OLF & its Dihydro- & Deglycosylated Congeners

Digoxin-free fresh-frozen human plasma was obtained from the American Red Cross (Louisville, Ky.). For serum samples not treated with SSA, we applied the whole 1-ml sample directly to the Sep-Pak cartridge. In both cases, to remove the $CH_3CN$ we evaporated the eluates to dryness, dissolved the residue in 1 ml $dH_2O$, and filtered the solution through a Whatman 0.22-$\mu$m polyvinylidene fluoride filter (PVDF) in preparation for HPLC.

Example 6

Molar Absorptivity & Concentration of OLF and Dh-OLF

UV spectral properties, molar absorptivity, and concentrations of these endogenous factors were calculated. At their individual maximum-absorbance wavelengths, the molar absorptivity of OLF and Dh-OLF was assumed to be comparable to those of ouabain and dihydroouabain (dho-B), respectively. Using the percentage cross-reactivities of OLF and Dh-OLF obtained by ouabain enzyme immunoassay (EIA) or dihydroouabain EIA, respectively, the apparent molar immunoreactive-concentration of both molecules were determined. The percent cross-reactivity of OLF and congeners with their respective antibodies were obtained from these data.

Example 7

Immunoreactive Measurement of OLF & Dh-OLF

OLF was measured using ouabain EIA. This assay uses ouabain covalently bound to the microtiter plate to compete with unbound samples or standards for binding to a constant amount of anti-ouabain antibody (Harris et al., 1991). Dihydroouabain-like immunoreactivity was measured by EIA using a polyclonal dihydroouabain-specific antibody prepared according to our specifications by HTI Bio-Product Inc (Ramona, Calif.). The antibody production strategy was as follows: dihydroouabain (dho) was conjugated to keyhole limpet hemocyanin (KLH) through the rhamnose sugar ring and the resulting conjugate was injected in three rabbits. Blood samples from the rabbits were drawn three weeks after the primary injection, and every two weeks after subsequent booster injections.

Immunoglobulins were further purified with ammonium persulfate precipitation followed by dialysis with phosphate buffer saline. The EIA assay was based on the competitive binding of bound dho with free (unbound) dho or sample to a constant amount of dho-antibody. The presence of dihydroouabain or sample in the microtiter well results in the reduction of the dho-antibody binding to the dho-coated microtiter well. This consequently caused a reduction of secondary antibody (goat anti-rabbit horseradish peroxidase conjugate) binding and therefore a decrease in the signal obtained from the breakdown of the substrate by the conjugated enzyme. The signal intensity is therefore inversely proportional to the amount of dho or Dh-OLF in the well.

Briefly, immunoassay plates were coated with approximately 0.5 µg dho-BSA conjugate/well for a minimum of 18 hrs. at 4° C. The plate was washed with 0.05% Tween-20 in PBS (wash solution) then blocked with a 10 g/l BSA solution in PBS (blocking solution) for 2 hours at 37° C. After washing, the standards and samples (50 µl/well) were first added followed by the addition of the dho-antibody (50 µl) and the plate was incubated at room temperature. After two hours, the plate was washed four times, blotted slightly, and 100 µl of the secondary antibody (a Goat anti-rabbit horseraddish peroxidase conjugate) was added and allowed to bind to the dho-antibody for additional two hours at room temperature. Finally, the plate was washed three times and 100 µl of substrate TMB soluble reagent was added to each well. Color development was monitored at 650 nm for a maximum of 30 min. after which the reaction was stopped with TMB Stop buffer and the plate was then read at 450 nm. The readings were adjusted with a system blank and for non-specific binding.

Example 8

Inhibition of $Na^+,K^+$-ATPase Activity (Inhibition of Sodium Pump)

This assay was used to measure the effect of mammalian OLF and its congeners on phosphate release in hydrolysis of ATP based on the method of Chan and Swaminathan (1992) with minor modifications to increase the sensitivity of the method for small volumes. Dried frozen powder of porcine cerebral cortical tissue (PCC) was reconstituted at 1 Unit/ml in buffer containing; 50 mM Tris-HCl and 2 mM $MgCl_2$, at a pH of 7.2. The reconstituted tissue was then washed three times and resuspended in the same buffer. The protein concentration was determined by BIO-RAD Protein Assay (Bio-Rad, Hercules, Calif.), adjusted to about 1 mg/ml and used both in the catalytic inhibition and ouabain-stimulated phosphorylation experiments (PAGE and Western analysis). The inhibition assay was performed briefly by pipetting 20 µl of sample containing the desired concentration of glycoside (Tris buffer was used for no-inhibitor control) into a well of a microtiter plate placed in a 37° C. water bath for 10 minutes. As a source of alpha subunit (all isoforms) of $Na^+,K^+$-ATPase, 20 µl of the porcine cerebral cortical $Na^+,K^+$-ATPase solution diluted in Tris buffer pH 7.8 (1 mg/ml) was added and allowed a further 20 minute-incubation. Twenty µl ATP solution (10 mM in Tris buffer pH 7.8) was added and allowed to react for 15 additional minutes. The final concentrations of the mix were as follows: potassium 3.3 mmol/, sodium 133.3 mmol/l, magnesium 3.3 mmol/l, and ATP 3.3 mmol/l, in Tris-HCl buffer, 133.3 mmol/l, pH 7.8. After the incubation period, we added 150 µl of molybdate solution (per liter, 1.0 mmol of molybdate, 11 mmol of sulfuric acid, and 142 ml of Tween 80: methanol solution (12:88 by vol). After 30 minutes of incubation, color development was allowed to proceed for a maximum of 30 min. after which the color intensity was measured by pipetting 150 µl of the reaction mixture from each well to a corresponding well on another microtiter plate. The color intensity is proportional to the release of phosphate ions which is a direct indicator of ATP breakdown and therefore NKA activity. The absorbances were measured simultaneously at 340 nm. The percent of $Na^+,K^+$-ATPase activity inhibition represents the ouabain inhibitable activity by the glycosides.

Example 9

Statistical Analysis

All samples were assayed three to five times. Duplicate samples were corrected for background (assay buffer only), averaged and normalized to ouabain sensitive $Na^+,K^+$-ATPase activity (100% inhibition at 1 mM ouabain). Each value represents the mean±standard deviation of the number of sample assays performed. The percent of $Na^+,K^+$-ATPase activity inhibition of each compound represents the proportion of ouabain activity that is inhibitable by that compound. The statistical analysis including a best-fit by logit-regression curves to determine the concentration of inhibitor required for 50% inhibition ($IC_{50}$) was performed on SPSS for windows, advanced statistical program version 7.5 (SPSS, Chicago, Ill.).

Example 10

Location of α-Isoforms of Sodium Pump

The location of the sodium pump ($Na^+,K^+$-ATPase) α-isoforms on the gel were determined by Western Blot analysis by utilizing NKA isoform-specific antibodies (UBI, Lake Placid, N.Y.) to the three α-isoforms. By aligning the location of the band on the X-ray film to the pre-stained molecular size markers on the dried gels, the location of each of these species was determined (unpublished data). SDS-PAGE was performed by the Laemmli method. Briefly, protein samples were diluted 5× in loading buffer (250 mM Tris-HCl, pH 6.8, 10% SDS, 3% β-mercaptoethanol, 50% glycerol, 0.01% bromophenol blue) and heated to 65° C. for 5 min. prior to loading on a duplicate of 7.5–12.5% SDS-PAGE gel. Electrophoresis was performed on a minigel SE 260 unit (Hoefer Scientific Instruments-San Francisco, Calif.). Duplicate SDS-PAGE gels were run each including a negative control and a pre-stained molecular size markers (BiORad, Hercules, Calif.). One gel was stained with bromophenol blue to visualize the separated bands, the other one was electrophoretically transferred by TE 42 Transphor Electrophoresis Unit (Hoefer Scientific Instruments-San Francisco, Calif.) to a 0.45 micron nylon membrane (MSI, Westboro, Mass.). The blotted proteins were probed for one hour with monoclonal anti-$Na^+,K^+$-ATPase α-1, α-2, and α-3 subunits antibodies (UBI, Lake Placid, N.Y.). The location of each isoform on the blot was visualized using a horseradish peroxidase-conjugated goat anti-mouse antibody and the signal was detected on an autoradiogram by chemiluminescence according to manufacturer's instruction (Amersham Life Sciences, Buckinghamshire, England).

Example 11

Ouabain-stimulated $^{32}P_1$ Phosphorylation of Na$^+$, K$^+$-ATPase

The ouabain-stimulated phosphorylation of Na$^+$, K$^+$-ATPase by phosphate was performed as described in Huang et al., (1994) with some minor modifications. Since the covalently phosphorylated intermediate of the sodium pump formed from inorganic phosphorous ($^{32}$Pi) is alkali-labile (acid-stable phosphenzyme intermediate), acidic pH gel electrophoresis was used to resolve the radioactively labeled protein species. Briefly, 60 μl aliquots containing 100–200 μg of porcine cerebral cortical tissues (PCC) were pre-incubated at room temperature for 25 min. with 20 μl of sample in the reaction buffer (50 mM Tris-HCL and 2 mM MgCl$_2$, pH 7.2). A positive control was pre-incubated with 20 μl of a 1 mM ouabain solution also, a negative control was pre-incubated with 20 μl of buffer alone. 10 μl of $^{32}$Pi (1 mCi in 100 μl) was diluted with 250 μl of phosphoric acid and purified through 0.2 μm filter to remove polyphosphates. At the end of the incubation, 20 μl of the $^{32}$Pi filtrate (30 μM, 8 uCi) was added to the mixture and allowed to incubate at room temperature for an additional 15 minutes. The reaction was terminated by the addition of 1 ml 8% HCLO$_4$ which precipitated the proteins and left unincorporated $^{32}$Pi in solution. The sample was then immediately pelleted and resuspended in sample buffer containing at a final concentration; 0.5% by volume HCLO$_4$, 2.5% by weight SDS, 10% by volume glycerol and 0.1% by weight pynomin Y dye. Samples (100 μl) were loaded on a 12% acid polyacrylamide gel and run at 4° C. for 4–5 hrs at a constant current of 30 mA. The gel was fixed in 40% methanol, 10% acetic acid, dried and autoradiographed. Autoradiograms were quantitated using a soft laser scanning densitometer.

Example 12

Discovery and Isolation of Dihydro-OLF (Dh-OLF)

In a previous report the inventors demonstrated a technique for isolation of several congeners of both DLIF and OLF in one chromatographic elution (Qazzaz et al., 1996a). Using that procedure, OLF migrated early in the elution profile, i.e. fraction at 6 min. The OLF fraction was further characterized here at 6 min using an isocratic mode of 10% CH$_3$CN in water. Under these conditions four well-resolved chromatographic peaks are resolved, which correspond to ouabain (at 30 min), ouabagenin (at 20 min), and two isomers of dihydroouabain (dho-A and dho-B) which elute at 24.5 and 27.5 min, respectively. The endogenous OLF fraction eluted at 6 min. from adrenocortical tissue further separated into three congeners, one previously identified as OLF-genin, and a new species with properties similar to those of dihydroouabain, herein called Dh-OLF. The Dh-OLF isolated herein at fraction 27.5 showed an identical chromatographic retention time to the standard dihydroouabain component dho-B. This new species of OLF was also found in isolates of human serum. In all cases, the elution profiles were monitored using immunoreactivities to both ouabain and dihydroouabain antibodies and absorbance at 196 nm.

Figure 13: Spectral Analysis and Concentrations of Dh-OLF & OLF

The UV spectra of Dh-OLF and OLF are similar to those of dihydroouabain (maximum at 196 nm) and ouabain (maximum at 222). The 196 nm $\lambda_{max}$ Dh-OLF is consistent with the presence of a chemically reduced (hydrogenated) lactone ring as shown above, including the far-UV shift and lower absorptivity, both characteristic of the hydrogenated lactone ring. To estimate the absolute and relative concentrations of the two OLF species, OLF and Dh-OLF, identical molar absorptivities to those of the plant-related compounds, ouabain and dihydroouabain (component dho-B), respectively were assumed. When similar extraction efficiencies are assumed between Dh-OLF and OLF, the following amounts and relative concentrations of Dh-OLF and OLF were found in bovine adrenal cortical tissue and in human serum. See Table 1 below.

TABLE 1

Amount of OLF and Dh-OLF in bovine adrenal cortex and human plasma

| Endogenous factor | Human serum (Moles × 10$^{-10}$/l serum) | Adrenal cortex (Moles × 10$^{-10}$/gm cortex) |
|---|---|---|
| OLF | 3.8 ± 0.42 (n = 4) | 0.017 ± 0.003 (n = 5) |
| Dh-OLF | 50 ± 4.6 (n = 5) | 0.360 ± 0.034 (n = 5) |

Similar molar absorptivities assumed between ouabain & OLF and dihydroouabain (dho-B) & Dh-OLF. The ratio of Dh-OLF to OLF in adrenal cortex and human serum are 22 and 13 respectively. Each value represents the mean ± standard deviation of number of tissue extractions performed.

Example 14

Immunoreactivity of DH-OLF & OLF

Two specific antibodies, one against ouabain and one against dihydroouabain, were used to characterize OLF and DH-OLF. Both of these antibodies are sensitive to structural changes at the lactone ring epitope of these molecules. Ouabain antibodies showed 2–3% cross-reactivity with dihydroouabain while dihydroouabain antibodies showed 0.1% cross-reactivity with ouabain. OLF and Dh-OLF showed a unity response in reactivity with ouabain antibody and dihydroouabain antibodies, respectively. The 50% response was used to compare their immunoreactive potencies as shown in figure 3. The concentrations were determined using molar absorptivities as described above.

Example 15

Na$^+$,K$^+$-ATPase Inhibitory Potencies of DH-OLF & OLF

The relative potencies for inhibition of Na$^+$,K$^+$-ATPase catalytic activity (porcine cerebral cortex containing three alpha isoforms) by ouabain and the standard isomer dho-B and by OLF and DH-OLF were compared. The concentrations of both OLF and Dh-OLF were determined by assuming comparable molar absorptivity between ouabain and OLE and between dihydroouabain (dho-B) and Dh-OLF. OLF is 12-fold more potent than ouabain, while Dh-OLF is 3-fold more potent than dihydroouabain component B (dho-B). The order of inhibitory activity also shows that OLP is 10-times more potent than Dh-OLF just as ouabain is more potent than dihydroouabain. The response curves of the mammalian-derived factors did not parallel those of the plant-related counterparts, which is an indication of potential differences in their binding due to isoform, tissue and organ specificities. Also, both Dh-OLF and its plant-related counterpart dho-B had response curves steeper than those of OLF and ouabain, which is an indication of different binding affinity of the compounds with reduced lactone ring vs. with the corresponding oxidized species.

Example 16

Phosphorylation of $Na^+$, $K^+$-ATPase by Dh-OLF & OLF

Ouabain-stimulated $^{32}Pi$-phosphorylation of the $Na^+,K^+$-ATPase alpha subunit has shown to be dependent on the binding of ouabain to its specific binding site on the alpha subunits. This phosphorylation incorporates Pi covalently into the same aspartyl amino acid of the α-subunit of $Na^+$, $K^+$-ATPase that is phosphorylated by ATP during ATP-hydrolysis). The phosphorylation of the alpha subunits was induced by the mammalian-derived OLF and Dh-OLF isolated from both bovine adrenal cortical tissue and human sera. Moreover, the incorporation of $^{32}Pi$ into the α-subunit, when stimulated by OLF and Dh-OLF, ws shown to be dependent on the concentration of these factors. The concentrations of Dh-OLF required for phosphorylation paralleled the concentration range of $Na^+,K^+$-ATPase required for catalytic inhibition. The inhibition of the sodium pump by ouabain or other plant-derived and endogenous pump inhibitors was translated into a decrease of ATP break-down. However, while other inhibition assays typically are affected by interference of other ATPases in the tissue such as the $Ca^{2+}$-ATPase, ouabain-stimulated phosphorylation is specific for the $Na^+$, $K^+$-ATPase. Dho is, in fact, 82% as potent in stimulating ouabain sensitive phosphorylation of the sodium pump as ouabain, in equimolar concentrations.

Example 17

Experimental Findings

A new molecular form of a mammalian ouabain-like factor has been found by the inventors, and reported here: dihydroouabain-like factor (Dh-OLF). This factor has analogy to dho-B, one of two dihydroouabain (dho) isomers also isolated by the present inventors. The presence of a ouabain-like factor with a hydrogenated (reduced) lactone ring (Dh-OLF) in bovine adrenal cortex and in human plasma was demonstrated by a chromatographic elution pattern, an absorption spectrum, binding with two antibodies: one specific for ouabain and one specific for dihydroouabain, the inhibition $Na^+,K^+$-ATPase catalytic activity, and the ouabain-stimulated phosphorylation of the $Na^+,K^+$-ATPase alpha subunit.

The HPLC patterns (order and time) of the endogenous pair, OLF and Dh-OLF, from bovine adrenals and human plasma are similar to those of their respective cardiac glycoside plant-derived counterparts, ouabain and dihydroouabain. Two isomers of plant-related dihydroouabain (dho-A and dho-B) were recently separated by the inventors and are included in a separate patent. While OLF and its deglycosylated congener are present in bovine adrenals and human plasma, one dihydroouabain-like (Dh-OLF) isomer was found in these tissues. The presence of Dh-OLF as the dihydro-species present in both bovine adrenals and human plasma was further confirmed and characterized using a dho-specific antibody. The uv spectra of the endogenous mammalian OLF and Dh-OLF from both tissues are similar to those of their respective counterparts, ouabain and dho-B, except that the $\lambda_{max}$ of ouabain and OLF are 220 nm, whereas dho and Dh-OLF have maximal absorbances at 196 nm. The $\lambda_{max}$ of Dh-OLF confirms that it has a reduced lactone ring, like the plant-derived hydrogenated derivatives, where two incorporated hydrogens replace the double bond of OLF. This characteristic absorbance peak is associated with the same uv shift observed in OLF and its plant-derived ouabain as seen from their chemical formulas above.

The two different antibodies used to further characterize OLF and Dh-OLF, anti-ouabain and anti-dihydroouabain antibodies, are sensitive to modifications to the lactone-ring of the ouabain and dihydroouabain molecules. Thus, while the anti-ouabain antibody had 100% affinity for ouabain, it showed little affinity for dihydroouabain or DhOLF. Similarly, the anti-dihydroouabain antibody had 100% and 0.1% affinity for dihydroouabain and ouabain and OLF, respectively.

The EIA data clearly showed the presence of a compound with a separate immunoreactive peak that was not "ouabain-like" but "dihydroouabain-like", and whose relative elution position correlated well with the absorbance spectrum characteristic of a reduced lactone ring cardenolide. In addition, the mammalian factor OLF and OLF-genin, the latter showing 60% cross-reactivity with ouabain for binding to the ouabain antibody, were detected as two separate immunoreactive peaks. These two peaks eluted from the HPLC at 19 and 30 minutes, respectively, on the same isocratic mode of 10% $CH_3CN$ in a deionized water mobile phase. This clearly shows that Dh-OLF exists in mammals and has analogy to one of the two dho isomers: dho-B. When assayed, OLF and Dh-OLF evidenced immunoreactivity with anti-ouabain and anti-dihydroouabain antibodies, respectively.

Table 1 above shows the Dh-OLF:OLF ratio in adrenal tissue to be 22, and the Dh-OLF:OLF ratio in human serum to be 13, almost one half of that found in adrenal cortex. Assuming similar extraction efficiencies, these data show the abundance of these two factors with respect to those of the mammalian dihydro-digoxin-like immunoreactive factor (Dh-DLIF) and its oxidized species digoxin-like immunoreactive factor (DLIF).

The molar ratio of Dh-DLIF to DLIF was found to be about 5.3 in bovine adrenocortical tissue and about 0.38 in human serum. This demonstrates that adrenocortical tissues contain higher amounts of both DH-DLIF and Dh-OLF, the hydrogenated species than of DLIF and OLF, their respective oxidized species. The ratio of Dh-OLF, the present factor, to OLF, however, is 4.2-times higher than that of Dh-DLIF to DLIF in adrenocortical tissues. This indicates that dihydro-OLF is acting as a precursor for OLF in the adrenal gland and, thus, that these glands maintain available a higher amount of the hydrogenated precursor for enzymatic regulation of the production of OLF, when needed for secretion into the blood stream. This conversion step provides a novel target drug development. Moreover, the ratio of Dh-OLF to OLF in plasma reflects changes in the extent of protein binding observed during pathology. The present observations show that OLF and Dh-OLF are present in different quantities and molar concentrations in different mammalian tissues, with the highest ratio of Dh-OLF to OLF being observed in the adrenal cortex. This reflects actual variations in the ratio of the reduced and oxidized forms of an agent involved in the metabolic regulation of in vivo production of OLF from Dh-OLF. It also evidences that a metabolic balance between OLF and Dh-OLF exists in different mammalian tissues, and that the balance varies depending on the physiological and pathological status of the individual.

Thus, the oxidized (OLF) and reduced (Dh-OLF) species of this mammalian factor were shown to be metabolically, physiologically and pathologically linked, with the adrenal glands being a rich source of these factors. As already indicated above, dihydro-digoxin is converted to a digoxin-like immunoreactive substance by microsomes prepared from bovine adrenal cortex. This occurs by an oxidation of the lactone ring mediated by cytochrome P-450, NADPH and a NADPH-dependent reductase.

Equivalent molar absorptivities may be assumed for OLF and Dh-OLF at their respective absorbance maxima, 220 nm and 196 nm respectively, and for ouabain and dihydroouabain, 220 and 196 nm respectively. Although a first order approximation, this assumption was used to estimate the molar concentration of each mammalian factor from their absorption values at the respective wave lengths. The ratio of actual OLF or Dh-OLF per ouabain or dihydroouabain immunoreactivity equivalent was calculated to be 1 pmol/1 pmol. That is, the relative molar-immunoreactivity of OLF and Dh-OLF when compared to the immunoreactivity of ouabain and dihydroouabain for their respective antibodies (anti-ouabain and anti-dihydroouabain antibodies) is one. When this value is compared to those of DLIF and Dh-DLIF, 975-fold and 2588-fold less immunoreactive than digoxin and dihydro-digoxin for their respective antibodies, these relative molar-immunoreactivity values show that OLF and Dh-OLF are structurally more similar to their plant-related ouabain and dihydroouabain-B (dho-B) isomer counterparts, respectively, than are DLIF and Dh-DLIF to plant-derived digoxin and dihydro-digoxin.

A wide range of concentrations have been noted for the ouabain-like factor (OLF) as measured in human plasma by different immunoassays, such as RIA, EIA, and RRA. The human plasma concentration of OLF ranges from 25 pM to 34–95 pM to 50–750 pM, to 55–168 pM, to 204 pM. The concentration of OLF found by the inventors is 5 nM, surprisingly higher than all prior reported, and was obtained by EIA measurements.

The data show that both OLF and Dh-OLF evidence biological activities. Both were shown to inhibit the catalytic porcine cerebral cortex $Na^+, K^+$-ATPase activity and to phosphorylate the $Na^+$, $K^+$-ATPase alpha-subunit. OLF and Dh-OLF were found to be 10- and 3-times more potent than ouabain and one of two dihydroouabain isomers (dho-B), respectively. The mammalian Dh-OLF and the plant-derived dho-B isomer however are, respectively, 10- and 3-times less potent than their oxidized species (OLF and ouabain). The difference in the ratios clearly show that both mammalian factors are far more potent than their plant-derived counterparts.

The results presented here, thus, show that Dh-OLF has a role in regulating the catalytic activity of the sodium pump in mammalian tissues. In addition, the naturally occurring mammalian Dh-OLF was shown to have a reduced inhibitory potency compared to the oxidized species (OLF). This effect is likely due to the presence of a reduced lactone ring in Dh-OLF.

Example 18

Purification and Characterization of Two Isomers of Dihydroouabain

Commercial samples of dihydroouabain were separated by HPLC as described in Example 4. Each of the two purified dihydroouabain isomers was dissolved in deuterated methanol ($CD_3OD$) and transferred to an NMR sample tube (Wilmad 327-PP). Preliminary $^1H$ and $^{13}C$ data were obtained in a Nalorac 3 mm Z-Spec MDB probe. Two dimensional NMR experiments ($^1H$-$^1HCOSY$, $_1H$-$_{13}C$ HMQC, HMBC) were performed with the 3 mm sample tube in 5 mm BB-inverse probe using the standard Bruker pulse sequences.

The mass spectral observations (the fragmentation pattern and relative ion abundance) obtained by positive-ion $ESI^+$ mass spectrometry indicates that the two components of dihydroouabain are molecular isomers. A single unique peak (the principal ion of the active material) observed at m/z (mass/charge ratio) 587.1 was identified as the protonated ion [$M+H^+$] in all three spectra. This ratio corresponds to the protonated ion of a substance of integer mass 586.7 Da identical to that expected for dihydroouabain. Similarly, identical signals observed at m/z 147 and 85 are identified as the sugar moiety and the lactone ring of dho, respectively. Overall, the two purified isomeric compounds gave identical fragmentation patterns to each other and to the dho stock. Both compounds have an elemental composition of ($C_{20}H_{46}O_{12}$). The theoretical accurate mass of both compounds is 587.8 Da as determined by ESI mass spectroscopy.

The two HPLC purified isomers of dho displayed early identical proton $^1H$ NMR spectra, both in chemical shift and in signal intensity. Two groups of proton resonances were observed to display noticeably different chemical shifts between the two isomers.

Due to slight structural and polarity changes brought about by the saturation of the C20–22 bond, both isomers of dho have uv-maximum absorbance at 196 nm, which is characteristic of saturated lactone rings on cardenolides. Despite the fact that HPLC was able to resolve these two components, mass-spectral analysis was unable to detect any structural difference between the two dho components. However, NMR data further supported the existence of isomerism. Although the two isomers revealed nearly identical proton NMR spectra, both in chemical shift and in signal intensity, two groups of proton resonances displayed remarkably different chemical shifts. The two isomers have been termed dhoA and dhoB.

Example 19

Similarity of dhoB to Dh-OLF

Although both dho-A and dho-B appear to be similar in immunoreactivity and enzymatic inhibitory activity, dho-B is more similar to the agent of this invention, based on its HPLA profile. While the differences between the two isomers reamins unelucidated, the closer similarity of dho-B to Dh-OLF seen on HPLC indicates that dho-B may be the immunogen and standard analyte of choice. A mixture of the two isomers may economically and conveniently be used as an immunogen, since antibodies raised to dho cross-react with Dh-OLF and antibodies raised to Dh-OLF cross-react to dho. Neither cross-reacts with ouabain or OLF. However, only dho-B coelutes on HPLC with Dh-OLF. Therefore, dho-B preferably should be used as an economical substitute to Dh-OLF as a standard analyte for estimation of Dh-OLF by quantitative HPLC.

Example 20

Reduction of Excess Levels of OLF and Dh-OLF

As has been explained above, mammals may occasionally experience deleteriously high levels of OLF and Dh-OLF.

An acute occurrence may occur either spontaneously or because of administration of exogenous OLF or Dh-OLF. Examples of the former include essential hypertension crises and pregnancy related conditions such as extremely high arterial pressure, preeclampsia and eclampsia. The need may arise for rapid reduction of these levels in order to prevent organ damage. The antibodies or more preferably, the antibody fragments, synthetic analogues such as aptomers, or most preferably, the $F_v$ fragment, may be administered. These fragments may be made by injecting a production animal such as a sheep or goat, with dho-B or Dh-OLF. Production of the polyclonal antibody can be enhanced by conjugating the target molecule to a carrier molecule that is non-immunogenic to the subject to be treated. The antibodies are digested with an proteinase, most preferably papain, and purified by affinity chromatography. The chromatography column may have conjugated to its solid substrate either dho or Dh-OLF. On passage through the column, all fragments save the $F_v$ fragments will pass through the column without binding. The pure $F_v$ fragments can then be eluted with saline solution and further purified by means common in the art to produce a non-pyrogenic, sterile, pharmacologically acceptable formulation.

The $F_v$ formulation is injected or infused into a patient suffering from excessive OLF or Dh-OLF. The fragments bind strongly to Dh-OLF, which is therefore sequestered and excreted by the kidneys. As Dh-OLF is removed, its equilibrium with OLF is shifted and OLF is converted to Dh-OLF. This conversion continues until levels of OLF and Dh-OLF are in an acceptable, non-toxic range.

Example 21

High Blood Pressure Cohorts' Selection

It is expected that low dosages of Dh-OLF will enhance the activity of the sodium pump and lower arterial pressure. Separate studies will include high blood pressure patients with 1) essential hypertension and 2) pregnancy induced or associated hypertension, and 3) thyroidism induced or associated hypertension. Hypertensive patients are divided into 2 groups, a test group and a control group that either (1) self administer a solution of Dh-OLF twice daily for several days, or (2) self administer only a solution without Dh-OLF. Volunteers are also divided into two groups and administered similar protocols. All patients' blood pressure is taken in the morning and the afternoon daily at pre-set times.

The blood pressure of the treated hypertensive patients is lowered when compared to the controls and maintained throughout the period of administration. No significant effect is seen in the volunteers.

Example 22

Ophthalmologic Cohorts' Selection

Cataract patients are divided into 4 groups, of which the first group self administers a solution of Dh-OLF twice daily for several days, the second group is infused by injection a solution of anti-Dh-OLF antibody once every several weeks. The remaining control groups self administer only the solution or are infused with a similar volume of solution without agent. The volunteers are also divided into two groups and administered similar protocols.

The patients' eyes are examined by medical personnel at pre-set times. The extent of cataract advancement is reduced in the treated cataract patients when compared to the controls.

Example 23

Male Sexual Dysfunction Cohorts' Selection

Sexually dysfunctional patients are divided into four groups that received the following treatments: (1) self administration of a solution of Dh-OLF twice daily for several days, (2) self administration of the solution without Dh-OLF, (3) are infused by injection a solution of anti-Dh-OLF antibody once every several weeks, or (4) are infused the solution without the antibody.

The volunteers are divided into two groups and administered similar protocols. The sexually dysfunctional patients are examined in the morning and afternoon daily at pre-set times.

The sexual dysfunctionality is reduced in the treated patients with respect to controls.

Example 24

Congestive Heart Failure Cohorts' Selection

Cardiac patients receive 4 different treatments: Group 1 self administers a solution of Dh-OLF twice daily for various days, Group 2 self administers the solution without the factor, Group 3 is infused by injection of a solution of anti-Dh-OLF antibody once every several weeks, and Group 4 is infused by injection of the solution without the factor at similar times.

The volunteers are divided into two groups and administered similar protocols. The heart rate for all patients is monitored by the patients daily.

The heart rate of the treated cardiac patients is reduced when compared to the cardiac patient controls.

Example 25

Alzheimer's Disease Cohorts' Selection

Four groups of patients diagnosed with Alzheimer's disease either (1) self administer a solution of Dh-OLF twice daily for various days, (2) self administer the solution only, (3) or are infused by injection a solution of anti-Dh-OLF antibody once, (4) infused only with solution. The volunteers are divided into two groups and administered similar protocols. The patients are monitored in the morning and afternoon daily at pre-set times.

The treated patients' behavior is improved when compared to the patients' controls.

Example 26

Serum Assay

A patient's serum is diluted 10 times (about 1–1000 times range) in borate buffer containing 3% BSA, 0.05% Tween 20, 0.02% Triton X-100 pH 8.3 by dispensing 270 $\mu$l buffer and 30 $\mu$l serum into disposable test tubes or disposable dilution plate and mixing thoroughly.

Mammalian Dh-OLF or dho standards are prepared in human serum to cover a range over 1 log of the expected concentration range, which includes high and low dilutions.

100 $\mu$l of each serum sample are then transferred to each well of the microtiter plate using a pipet, the plate covered with a disposable plate sealer to minimize evaporation and incubated for 2 hours at 28° C. (2–24 hours at 4–28° C.). Each plate sealer is then removed and unreacted serum aspirated off using a microplate washer. The well is then washed with wash buffer for 5 seconds and the buffer is aspirated off the well. This procedure is repeated 2 additional times.

100 µl reaction mixture containing 0.5 mM fluorescently-labeled anti-Fc polyclonal antibody in 50 mM Tris-HCl buffer pH 7.8 with 10 mM $MgCl_2$ and 1.0 mM dithiothreitol are then dispensed into each well, and the reaction run for 30 minutes at 37° C. and stopped with 1 ml sodium borate buffer, pH 9.0. The fluorophore is then induced to fluoresce with 335 nm/410 nm excitation/emission wavelengths. Finally, a "0" calibrator value (control) is subtracted from the fluorophore's fluorescence value, fluorescence values of samples of known Dh-OLF concentration are plotted on a standard curve and the amount of Dh-OLF in each serum sample determined by interpolation from the standard curve.

We claim:

1. A purified mammalian dihydroouabain-like factor (Dh-OLF) having binding reactivity with antibody raised against dihydroouabain (dho).

2. The factor of claim 1 having less than about 2–3% binding reactivity with the antibody raised to plant-derived ouabain or mammalian ouabain-like sodium pump inhibitory factor (OLF).

3. The factor of claim 1 having 10-fold lower potency than OLF and 3-fold higher potency than dho for inhibiting sodium pump activity.

4. The factor of claim 1 which is human origin.

5. The factor of claim 1 which is of bovine origin.

6. The factor of claim 1 which is obtained by reduction of OLF.

7. A pharmaceutical composition comprising the mammalian Dh-OLF factor of claim 1 and pharmaceutically or veterinarily acceptable carrier.

8. The composition of claim 7 in the form of a formulation selected from the group consisting of oral, parenteral, ophthalmic, slow release and enteric coating formulations.

* * * * *